(12) United States Patent
Crocker

(10) Patent No.: US 9,254,851 B2
(45) Date of Patent: Feb. 9, 2016

(54) SENSOR ASSEMBLY

(75) Inventor: Robert Crocker, Derby (GB)

(73) Assignee: Sperry Rail International Limited, Trent House, RTC Business Park, London Road, Derby (GB)

( * ) Notice: Subject to any disclaimer, the term of this patent is extended or adjusted under 35 U.S.C. 154(b) by 675 days.

(21) Appl. No.: 12/812,326

(22) PCT Filed: Jan. 9, 2009

(86) PCT No.: PCT/GB2009/000049
§ 371 (c)(1),
(2), (4) Date: Nov. 3, 2010

(87) PCT Pub. No.: WO2009/087385
PCT Pub. Date: Jul. 16, 2009

(65) Prior Publication Data
US 2011/0043199 A1 Feb. 24, 2011

(30) Foreign Application Priority Data
Jan. 10, 2008 (GB) .................................. 0800406.1

(51) Int. Cl.
*G01R 33/12* (2006.01)
*B61K 9/10* (2006.01)
*G01N 27/90* (2006.01)

(52) U.S. Cl.
CPC .............. B61K 9/10 (2013.01); G01N 27/9033 (2013.01)

(58) Field of Classification Search
CPC ........ G01N 27/82; G01V 1/523; G01L 3/102; G01S 17/88; G01R 31/315
USPC ................................................. 324/217–220
See application file for complete search history.

(56) References Cited

U.S. PATENT DOCUMENTS

| | | | |
|---|---|---|---|
| 2,337,148 A | | 12/1943 | Barnes |
| 2,356,967 A | | 8/1944 | Barnes et al. |
| 2,671,197 A | | 3/1954 | Barnes et al. |
| 4,510,447 A | * | 4/1985 | Moyer ........................... 324/225 |
| 4,885,710 A | * | 12/1989 | Hersberger et al. ............ 702/146 |
| 5,081,745 A | * | 1/1992 | Siegenthaler ................ 19/159 R |
| 6,604,421 B1 | * | 8/2003 | Li .................................... 73/636 |
| 7,849,748 B2 | * | 12/2010 | Havira ............................ 73/639 |
| 7,882,842 B2 | * | 2/2011 | Bhat et al. ...................... 128/899 |

(Continued)

FOREIGN PATENT DOCUMENTS

| EP | 0844162 A1 | 5/1998 |
|---|---|---|
| EP | 1132735 A1 | 9/2001 |

(Continued)

OTHER PUBLICATIONS

Great Britain Search Report for Application No. GB0800406.1, dated Apr. 22, 2008.
International Search Report for PCT/GB2009/000049 dated Aug. 13, 2009.

*Primary Examiner* — Melissa Koval
*Assistant Examiner* — Trung Nguyen
(74) *Attorney, Agent, or Firm* — McCormick, Paulding & Huber LLP

(57) ABSTRACT

The invention relates to a means of enabling inspection of engineering components, such as rails used in the railway industry.

A rail inspection device comprises a sensor (24) and a compliant spacer (26). The compliant spacer (26) has an inner surface and outer surface. The sensor (24) is urged against the inner surface of the spacer (26) and, when in use, the outer surface of the spacer (26) is in contact with the rail under inspection.

11 Claims, 3 Drawing Sheets

(56) References Cited

U.S. PATENT DOCUMENTS

| | | |
|---|---|---|
| 2003/0020469 A1 | 1/2003 | Katragadda et al. |
| 2006/0006848 A1* | 1/2006 | Kliman et al. ............... 322/99 |
| 2006/0065055 A1 | 3/2006 | Barshinger et al. |
| 2009/0261979 A1* | 10/2009 | Breed et al. ............... 340/576 |
| 2012/0189410 A1* | 7/2012 | Toebes et al. ............... 414/273 |

FOREIGN PATENT DOCUMENTS

| | | |
|---|---|---|
| EP | 1783501 A2 | 5/2007 |
| GB | 359432 A | 10/1931 |
| GB | 941457 A | 11/1963 |
| JP | 02055086 A | 2/1990 |
| JP | 11183441 A | 7/1999 |

* cited by examiner

SENSOR ASSEMBLY

CROSS REFERENCE TO RELATED APPLICATIONS

This application claims the priority of PCT application no. PCT/GB2009/000049, which was filed Jan. 9, 2009, and Great Britain application no. 0800406.1, which was filed on Jan. 10, 2008, and of which the entire disclosures are hereby incorporated by reference.

FIELD OF THE INVENTION

The present invention is directed to a means of enabling inspection of engineering components, such as rails used in the railway industry, using various sensors that make use of electromagnetic effects.

BACKGROUND OF THE INVENTION

Engineering components which are electrical conductors can be inspected using electromagnetic techniques. These include but are not limited to eddy current inspection, magnetic flux leakage, residual magnetism, alternating current flow measurement (acfm), and magnetic induction.

All of these techniques rely on either an electromagnetic or magnetic field to be created in the vicinity of the surface of the component. The sensor then measures either the absolute properties of the field, or far more commonly, variations of those properties as a function of the spatial relationship between sensor and surface position. Typically the sensor will be scanned across the surface of the component either by moving the sensor with respect to the component or vice versa. As this relative movement occurs the interaction between the sensor and the field is monitored. Variations in the material of the component close to its surface will then be revealed as local disturbances of the field.

This type of technique has found wide application in many fields of engineering and there are many instances of proprietary equipment that carry out such inspections routinely. The most important uses are for the detection of surface breaking cracks, and in some cases non-surface breaking but close-to-surface cracks. Other uses are in material sorting to differentiate one type of material from another.

FIG. 1 shows a system, indicated generally by the reference numeral 1, in which the principles described above are applied. The system 1 comprises a component under inspection 2, a sensor 4, and a non-magnetic spacer 6. In use, the spacer 6 and the sensor 4 move relative to the component 2. The spacer is sized to provide the appropriate spacing between the sensor 4 and the component 2. In some exemplary applications, the separation is typically required to be of the order of about 1 or 2 millimeters for the sensor to maintain the appropriate sensitivity.

FIG. 2 shows a system 10 that is a variant of the system 1 described above. The system 10 comprises a component under inspection 12 and a sensor 14 similar to the component 2 and sensor 4 described above. The system 10 also comprises a mechanical arrangement 16 adapted to separate the component 12 and the sensor 14. In use, the mechanical arrangement 16 (and therefore also the sensor 14) moves relative to the component 12. The separation might typically be required to be of the order of about 1 or 2 millimeters for the sensor to maintain the required sensitivity.

Whilst the techniques described above can be very successful, they suffer from a common significant drawback. The response of the sensor is affected by two things: firstly the variation in the properties of the surface in the vicinity of the sensor, as described briefly above, but secondly the separation of the sensor and the surface under inspection. This latter parameter is often referred to as lift-off.

If the surface under inspection is well-controlled and of uniform and regular shape the sensor can be maintained easily at a known distance from the surface, typically less than 1 mm. However, any variations in this separation will cause variations in the nature and magnitude of the response of the sensor so that any variations in the shape or morphology of the surface will cause significant variations in the output of the sensor. These variations commonly dominate those caused by the material variations.

Consequently a great deal of effort has to be applied to establish a mechanical situation that controls this separation and the effects of lift-off. Conversely, where it is impossible to control the mechanical relationship it is often difficult to produce a satisfactory inspection regime. Thus if any component under inspection is subject to unknown amounts of wear which alter its shape then the results of one of these inspections can be unreliable because of the unknown effects of the consequent variation in lift-off.

Many systems make use of mechanical contact between sensor and component to control this separation but these invariably suffer from wear and the potential for damage where there are unexpected variations in the shape of the component.

The present invention seeks to overcome or address one or more of the problems identified above.

SUMMARY OF THE INVENTION

The present invention provides a device comprising a compliant spacer and a sensor (or a plurality of sensors), wherein the spacer has an inner surface and an outer surface and the sensor is urged against the inner surface of said spacer such that, in use, the outer surface of the spacer is in contact with an object under inspection. Preferably, the device is a rail inspection device. Preferably, the object under test is a rail.

The present invention also provides a method comprising the step of: providing a compliant spacer; mounting a sensor (or a plurality of sensors) such that it urges against an inner surface of the spacer; and positioning the spacer such that an outer surface of the spacer is in contact with an object under inspection. Preferably, the method is a method of rail inspection. Preferably, the object under inspection is a rail.

In use, the sensor is in contact with the inner surface of the spacer at the point where the outer surface of the spacer is in contact with the object under inspection.

The present invention enables the separation of the sensor and the component under inspection to be maintained at a constant magnitude set by the thickness of the spacer. In some embodiments of the invention, that dimension might be of the order of 1 mm to 2 mm; in other embodiments, that dimension might be less than 1 mm.

Since the spacer is compliant, the spacer conforms to the shape of the object under inspection. Thus, the provision of a compliant spacer facilitates the constant separation of the sensor and the component being inspected even where the exact shape of the surface is unknown and where the relative velocity of movement of sensor and component is high. The nature of the device is such that the separation is maintained at a constant magnitude but without the limiting effect of wear and mechanical damage.

In this manner, the present invention addresses one of the main difficulties in successful inspection of engineering components which is the variation in separation of sensor and component. A further advantage of the new device is the mechanical protection afforded to the sensor as the sensor is moved across the component and encounters mechanical protuberances.

The said spacer may be circular and the sensor may be positioned inside the circle. In one preferred embodiment of the invention, the spacer is a tyre. Preferably, the space is rotatable. Preferably, the spacer is arranged such that, in use, it is rolled along the device under test.

The sensor may be spring loaded or mounted on a spring loaded mechanism. In this manner, the spring is urged towards the inner surface of the spacer and hence towards the object under inspection. Thus, as the spacer flexes, the sensor remains in contact with the inner surface of the spacer.

The spacer may be urged against the object under inspection.

The sensor may be an electromagnetic sensor. Further, the sensor may measure the variation in the electromagnetic properties of the surface of the object under inspection in the vicinity of the sensor. By way of example, the electromagnetic properties being measured may be eddy currents. The spacer may be non-metallic. The object under inspection may be electrically conducting.

In one form of the invention, the object under inspection is a railway rail. The sensor may, for example, be used to detect defects in such a railway rail.

The spacer and the associated sensor may be moved relative to the object under inspection in order for measurements to be taken along said object. Preferably, the spacer is rotated along the said object. In an alternative arrangement, the object under inspection may be moved relative to the sensor.

BRIEF DESCRIPTION OF THE DRAWINGS

Embodiments of the invention will now be described with reference to the accompanying schematic drawings of which:
 a.

DESCRIPTION OF THE PREFERRED EMBODIMENTS

Figure 1:
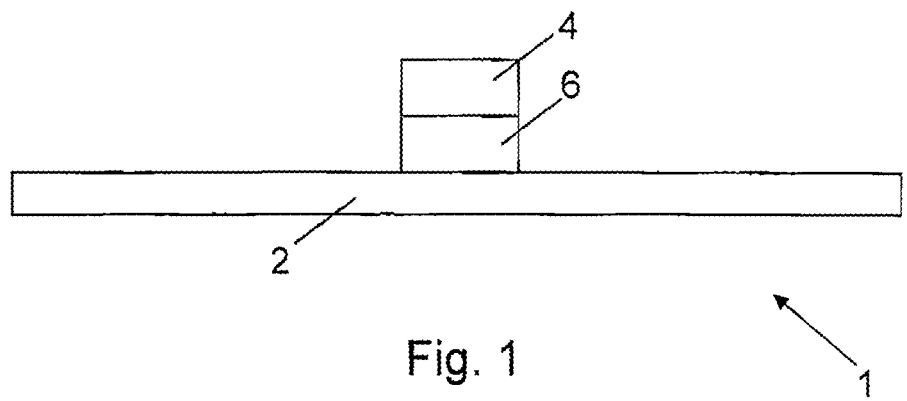
FIG. 1 is a cross-section of a known sensor arrangement;
 b.
Figure 2:
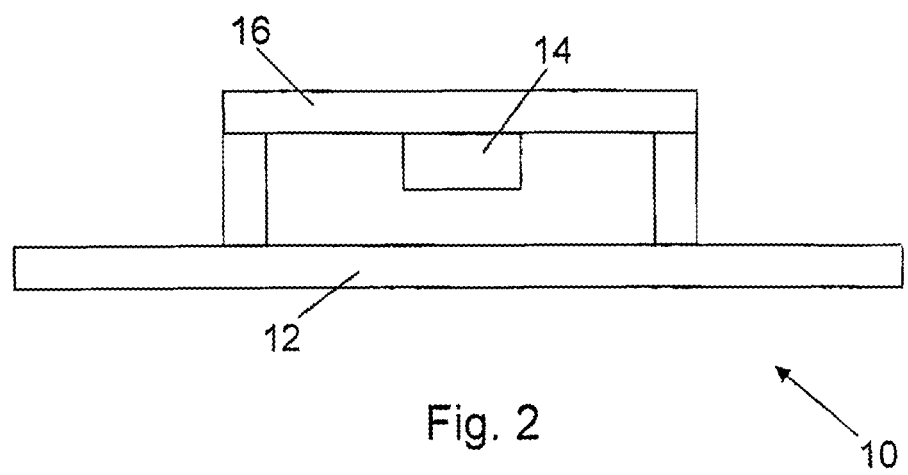
FIG. 2 is a cross-section of another known sensor arrangement;
 c.
Figure 3:
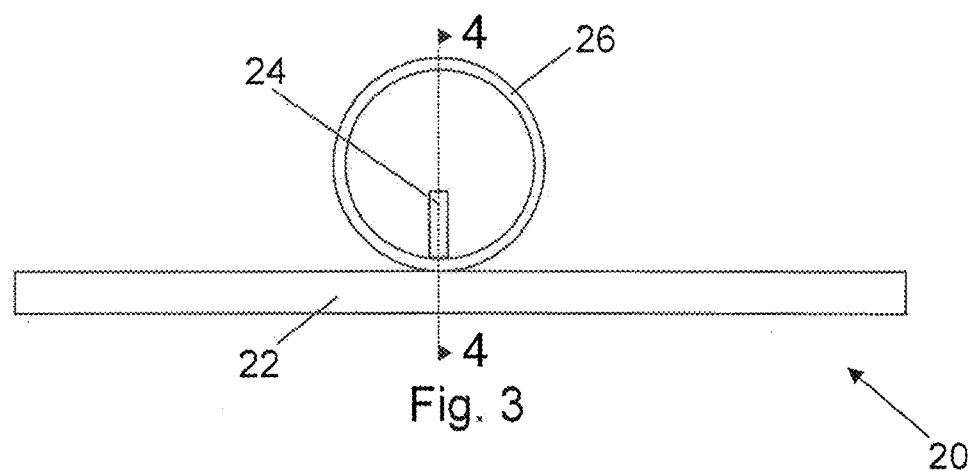
FIG. 3 shows a sensor arrangement in accordance with an aspect of the present invention;
 d.
Figure 4:
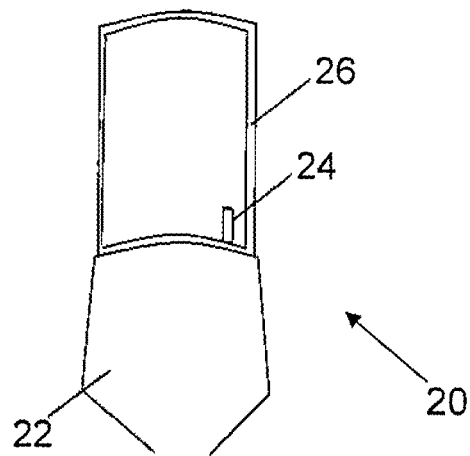
FIG. 4 demonstrates a use of the present invention;
 e.

FIGS. 3 and 4 show a system, indicated generally by the reference numeral 20. The system 20 comprises a rail 22, one or more sensors 24, and a compliant tyre 26. The tyre is urged against the rail 22 and, since the tyre is compliant, the tyre conforms to the shape of the rail.

The sensors 24 are mounted inside the tyre 26 such that the sensors are in contact with the inside surface of the tyre at the point where the outside of the tyre is in contact with the rail 22, as shown in FIG. 3.

The sensors 24 are mounted on a sprung loaded device which presses the sensors against the inside of the tyre such that as the tyre flexes, the sensors remain in contact with the inside surface.

An advantage of the sensor arrangements described above with reference to FIGS. 3 and 4 is that the sensors can make reliable measurements, even when the object under inspection is worn through use, as explained further below.

Figure 5:
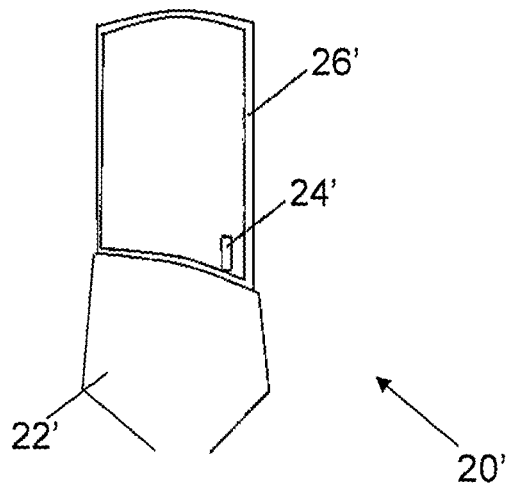
FIG. 5 demonstrates a use of the present invention when an object under inspection has been worn through use; and
 f.

FIG. 5 shows a system, 20' that is identical to the system 20 described above, with the exception that the rail 22' has become worn through use. As shown in FIG. 5, the compliance of the tyre 26' enables the tyre to take up the shape of the rail 22' in the transverse direction and because the sensor 24' is in contact with the inner surface of the tyre, the sensor remains a fixed distance from the surface, i.e. at the thickness of the tyre. Thus, if the shape of the rail changes as the tyre moves along it, the compliance of the tyre enables the shape to be followed and the sensors follow the tyre thus remaining at the same separation throughout the change of shape. Thus the effects of lift-off are largely eliminated.

Figure 6:
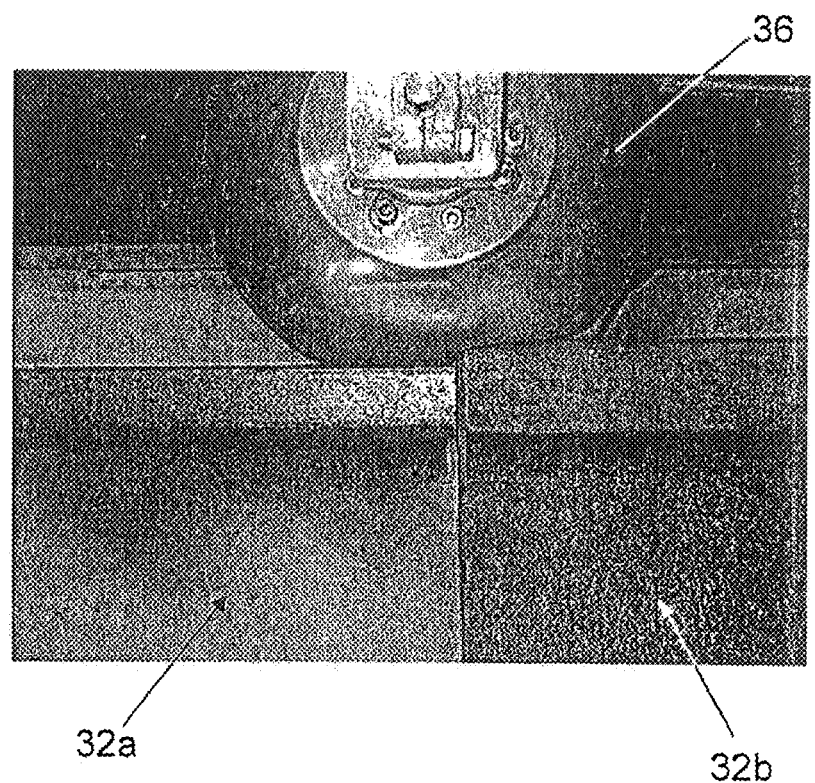
FIG. 6 demonstrates a further feature of the use of the present invention.

FIG. 6 shows the use of the present invention in a situation where a first rail 32a and second rail 32b meet. As shown in FIG. 6, the second rail is positioned slightly higher than the first rail; of course, such a scenario is common in practice. A sensor (not shown) is mounted inside a compliant tyre 36. Since the tyre 36 is compliant, it adjusts to the change in the shape of the components being measured as shown in FIG. 6.

The join between two rails, as shown in FIG. 6, causes considerable difficulty for conventionally mounted sensors. For example, sensors are often damaged when the sensor arrangement moves from being over the first sensor to being over the second sensor. At best, the difference in height can cause significant variation in lift-off. In the case of the device of the present invention, the tyre accommodates these shape changes by flexing as it rolls over them thus providing constant separation but also mechanical protection for the sensor on the inside surface.

The invention claimed is:

1. An inspection device for a rail of a railway comprising:
 a circular compliant spacer having an inner surface and an outer surface, wherein the circular compliant spacer is a tire configured to roll along a rail under inspection; and
 a spring-loaded electromagnetic sensor positioned inside the circular compliant spacer, wherein the sensor is urged into contact with the inner surface of the circular compliant spacer and toward the rail under inspection, and
 wherein, in use, the outer surface of the circular compliant spacer is in rolling contact with the surface of the rail under inspection.

2. The device according to claim 1, wherein the circular compliant spacer is non-metallic.

3. The device according to claim 1, wherein the sensor is configured to measure a variation in an electromagnetic property of the surface of the object under inspection in the vicinity of the sensor.

4. The device according to claim 1, wherein the rail under inspection is electrically conducting.

5. The device according to claim 1, wherein the spacer is rotatable.

6. A method of inspecting a metal rail of a railway comprising:
 providing a circular compliant spacer having an inner surface and an outer surface;
 mounting an electromagnetic sensor in a spring-loaded arrangement within the circular compliant spacer such that the sensor is urged against an inner surface of the circular compliant spacer; and
 positioning the circular compliant spacer such that the outer surface of the circular compliant spacer is in rolling contact with a rail under inspection.

7. The method of claim 6, further comprising driving the circular compliant spacer and the electromagnetic sensor relative to the rail under inspection.

8. The method of claim 7, wherein the circular complaint spacer is rotated along the rail under inspection.

9. The method of claim 6, further comprising using the sensor to measure a variation in at least one electromagnetic property of a surface of the rail under inspection in a vicinity of the sensor.

10. The inspection device of claim 1, further comprising a drive mechanism,
   wherein the drive mechanism is adapted to drive the circular compliant spacer and the sensor relative to the rail under inspection.

11. An inspection device for a metal rail of a railway comprising:
   a circular compliant spacer having an inner surface and an outer surface; and
   a spring-loaded electromagnetic sensor positioned inside the circular compliant spacer,
   wherein the spring-loaded electromagnetic sensor is urged against the inner surface of the circular compliant spacer, and
   wherein the outer surface of the circular compliant spacer is adapted to conform to an uneven surface of a rail under inspection.

\* \* \* \* \*